United States Patent [19]

Konrad et al.

[11] Patent Number: 4,684,371

[45] Date of Patent: Aug. 4, 1987

[54] OXIDATION HAIR DYES COMPRISING M-PHENYLENEDIAMINE DERIVATIVES AS COUPLING COMPONENTS

[75] Inventors: Günther Konrad, Hilden; Norbert Maak, Neuss; Edgar Lieske, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 814,062

[22] Filed: Dec. 19, 1985

Related U.S. Application Data

[63] Continuation of Ser. No. 578,186, Feb. 8, 1984, abandoned, which is a continuation-in-part of Ser. No. 252,596, Apr. 9, 1981, abandoned.

[30] Foreign Application Priority Data

May 2, 1980 [DE] Fed. Rep. of Germany ....... 3016881

[51] Int. Cl.$^4$ .............................................. A61K 7/13
[52] U.S. Cl. ........................................... 8/408; 8/411
[58] Field of Search .................................... 8/408, 411

[56] References Cited

U.S. PATENT DOCUMENTS

| | | | |
|---|---|---|---|
| 2,181,057 | 11/1939 | Krzikalla | 562/433 |
| 2,603,659 | 7/1952 | Raasch | 562/433 |
| 3,861,868 | 1/1975 | Milbrada | 8/424 |
| 4,125,367 | 11/1978 | Bugaut I | 8/407 |
| 4,185,958 | 1/1980 | Bugaut et al. | 8/405 |
| 4,286,989 | 9/1981 | Kadehjian et al. | 260/166 |
| 4,323,360 | 4/1982 | Bugaut et al. | 8/406 |
| 4,324,553 | 4/1982 | Bugaut et al. | 8/406 |
| 4,420,637 | 12/1983 | Bugaut II | 8/406 |
| 4,452,603 | 6/1984 | Konrad et al. | 8/407 |
| 4,566,876 | 1/1986 | Brown et al. | 8/411 |

FOREIGN PATENT DOCUMENTS

| | | | |
|---|---|---|---|
| 0029964 | 6/1981 | European Pat. Off. | 8/408 |
| 2758735 | 4/1979 | Fed. Rep. of Germany | 8/411 |
| 8001241 | 6/1980 | PCT Int'l Appl. | 8/408 |

OTHER PUBLICATIONS

Weissberger, D. G., vol. 652, p. 289 (1951).

*Primary Examiner*—Albert T. Meyers
*Assistant Examiner*—John M. Kilioyno
*Attorney, Agent, or Firm*—William H. Dippert

[57] ABSTRACT

This invention is directed to m-phenylenediamine derivatives and salts thereof and to compositions of the developer-coupler type of the dyeing of hair, consisting essentially of m-phenylenediamine derivatives or salts thereof as coupling components and, as developer components, conventional components used in oxidation dyes.

5 Claims, No Drawings

4,684,371

OXIDATION HAIR DYES COMPRISING M-PHENYLENEDIAMINE DERIVATIVES AS COUPLING COMPONENTS

CROSS-REFERENCE TO RELATED APPLICATION

This application is a continuation of U.S. patent application Ser. No. 578,186, filed Feb. 8, 1984, now abandoned, which in turn is a continuation-in-part of copending U.S. patent application Ser. No. 252,596, filed Apr. 9, 1981, now abandoned.

FIELD OF THE INVENTION

This invention is directed to oxidation hair dyes. More specifically, this invention is directed to m-phenylenediamine derivatives and their use as coupling components in oxidation hair dyes.

BACKGROUND OF THE INVENTION

Dyes known as oxidation dyes, which are produced by oxidative coupling of a developer component with a coupling component, are preferred due to their intense colors and very good fastness. Nitrogen bases such as p-phenylenediamine derivates, diaminopyridines, 4-aminopyrazolone derivatives, and heterocyclic hydrazones are generally used as developer substances. Phenols, m-phenylenediamine derivatives, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair, which capacity ranges from sufficient to very good; and, in addition, they should be toxicologically and dermatologically safe. The production of the strongest possible color shades closely corresponding to the natural hair color nuances is also important. Further, the general stability of the dyestuff produced as well as their fastness to light and to washing and their thermostability, have very special significance for the prevention of color shifts from the original color nuance or even a change in color to different shades.

Thus, the search for suitable oxidation hair dyes includes the task of finding the proper components that meet the above-mentioned prerequisites in an optimal fashion.

OBJECT OF THE INVENTION

It is an object of the invention to provide novel m-phenylenediamine derivatives.

It is also an object of the invention to provide agents for the oxidative dyeing of hair that are based upon m-phenylenediamine derivatives as coupling components.

It is a further object of the invention to provide a novel hair dyestuff composition of the developer-coupler type which imparts a blue nuance.

It is a yet further object of the invention to provide a process for dyeing hair wherein a novel hair dyestuff is employed.

These and other objects of the invention will become more apparent in the discussion below.

DETAILED DESCRIPTION OF THE INVENTION

Applicants have found novel hair dyestuffs that satisfy the above-mentioned requirements for good oxidation dyestuffs. The hair dyestuffs are based upon oxidation dyes comprising m-phenylenediamine derivatives of the formula

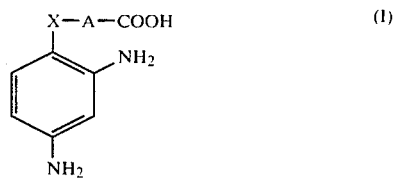

wherein X represents an oxygen or a single bond and A represents an alkylene radical of from 1 to 4 carbon atoms, or the alkali metal, alkaline earth metal, or ammonium salts thereof, as coupling component, and, as developer component, one or more of the conventional developer substances used in oxidation hair dyes. Such hair dyestuffs can meet the above-mentioned requirements to an especially high degree and consequently represent especially valuable combinations in the area of oxidation hair dyes. In addition, the hair dyestuffs according to the invention are particularly valuable because they provide blue nuances with p-phenylenediamine derivatives, preferably p-toluylene-diammonium sulfate and N-ethyl-N-(2-hydroxy-etyhl)-1,4-phenylenediamine sulfate (monohydrate), which nuances are especially desirable and useful in the dyeing of hair.

The invention also relates to a process for the preparation of the compounds of Formula I in which compounds of the formula

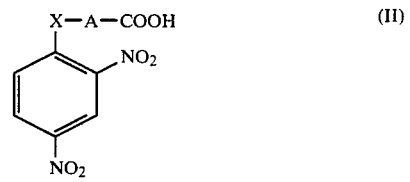

wherein X and A are as defined above, are reacted with hydrogen by a well-known method, in the presence of a catalyst.

The 2,4-dinitrophenyl compounds used as starting material for the preparation of the m-phenylenediamine derivatives of Formula I are a known class of substances. They can be prepared according to, or analogously to, methods known from the literature. See, for example, Gass. Chim. Ital, 22 I: 242, 1892; Ber. 13: 1680, 1880; Ber. 40: 1596, 1907; Ber. 42: 1310, 1909; and J. Med Chem. 11: 424, 1968, al of which are incorporated herein by reference.

The reduction of the compounds of Formula II with hydrogen takes place in the presence of hydrogenation catalysts such as palladium, for example, precipitated on active charcoal, generally without the addition of exogenous heat.

As mentioned above, A represents an alkylene radical of from 1 to 4 carbon atoms. Preferably A represents an alkylene radical of from 1 to 3 carbon atoms, and especially preferably A represents an alkylene radical of 1 or 2 carbon atoms. Thus, A may represent, for example, a methylene, ethylene, methylmethylene, dimethylmethylene, propylene, 1-methylethylene, 2-methylethylene, butylene, 1-methylpropylene, or 1,1-dimethylethylene group.

Additional aspects of the invention comprise the use of the m-phenylenediamine derivatives of Formula I as such, or in the form of their ammonium, alkali metal, or alkaline earth metal salts, as coupling components in oxidation hair dyes as well as hair dyes that contain the m-phenylenediamine derivatives of Formula I or their salts.

Upon the use of the compounds according to the invention, that is, the m-phenylenediamine derivatives of Formula I and the salts thereof, as coupling components together with developers generally used for oxidation hair dyes, the resulting hair dyes yield very intense shades in the blue and violet range, especially the blue range, and thus such use represents a considerable expansion of the possibilities in oxidation hair dyeing. In addition, the compounds according to the invention are characterized by very good fastness characteristics of the resulting colors, good solubility in water, good shelf-life, and toxicological as well as dermatological safety.

Hair dyes comprising oxidation hair dyes with a content of m-phenylenediamine derivatives of Formula I and/or their ammonium, alkali metal, or alkaline earth salts and of the developer substances normally used in oxidation hair dyes are consequently especially valuable compositions in the area of oxidation hair dyes.

Examples of the m-phenylenediamine derivatives according to the invention include the following: 2,4-diaminophenylacetic acid, 2,4-diaminophenoxyacetic acid, 3-(2,4-diaminophenyl)-propionic acid, 3-(2,4-diaminophenoxy)-propionic acid, 2-(2,4-diaminophenyl-butyric acid, 4-(2,4-diaminophenyl)-butyric acid, and 4-(2,4-diaminophenoxy)-butyric acid.

The developer components to be used according to the invention are generally those that are conventionally used in oxidatively coupled dyestuffs. Examples of such developer components include primary aromatic amines with an additional functional group in the p-position, such as p-phenylenediamine, p-toluylenediamine, p-aminophenol, N-methyl-p-phenylenediamine, N,N-dimethyl-p-phenylenediamine, N,N-diethyl-p-phenylenediamine, N,N-diethyl-2-methyl-p-phenylenediamine, N-ethyl-N-hydroxyethyl-p-phenylenediamine, N,N-bis-($\beta$-hydroxyethyl)-amino-p-phenylenediamine, methoxy-p-phenylenediamine, 2-chloro-p-phenylenediamine, 2,6-dichloro-p-phenylenediamine, 2-chloro-6-bromo-p-phenylenediamine, 2-chloro-6-methyl-p-phenylenediamine, and 6-methoxy-3-methyl-p-phenylenediamine, and other compounds of this type which also contain one or more additional functional groups such as hydroxyl groups, amino groups, or —NHR or —NR$_2$ groups, in which R represents an alkyl or a hydroxyalkyl moiety with from 1 to 4 carbons. Diaminopyridine derivatives, heterocyclic hydrazone derivatives such as 1-methyl-pyrrolidon-(2)-hydrazone, 4-amino-pyrazolone derivatives such as 4-amino-1-phenyl-3-carbamoylpyrazolone-5, and N-butyl-N-sulfobutyl-p-phenylenediamine are additional examples of useful developer components.

Further developer components that can be used according to the invention include tetraaminopyrimidines of the general formula

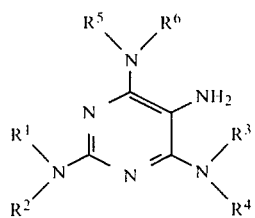

wherein $R^1$ to $R^6$ may each be a hydrogen atom; an alkyl moiety with from 1 to 4 carbon atoms; or the radical —(CH$_2$)$_n$x in which n is an integer of from 1 to 4 and X is selected from the group consisting of a hydroxyl group, a halogen atom, and —NR$^7$R$^8$ in which R$^7$ and R$^8$ are each a hydrogen atom or an alkyl group having from 1 to 4 carbon atoms or together with the nitrogen atoms R$^7$ and R$^8$ form a member selected from the group consisting of a 5 or 6-membered heterocyclic ring optionally containing an additional nitrogen atom or oxygen atom in the ring, as well as their inorganic or organic salts.

The tetraaminopyrimidines to be used as developer components may be used as such or in the form of their salts with inorganic or organic acids, such as, for example, chlorides, sulfates, phosphates, acetates, propionates, lactates, citrates, and the like.

Developer substances suitable for combination with the bis-(2,4-diaminophenoxy)-alkanol coupling components according to the invention also include, for example, the following:

2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5-diamino-6-methylamino-2-piperidinopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-$\beta$-hydroxyethylaminopyrimidine,
4,5,6-triamino-2-$\beta$-amino-ethylaminopyrimidine,
2,5,6-triamino-4-$\beta$-methylamino-ethylaminopyrimidine, 2,5-diamino-4,6-bis-γ-diethylamino-
propylaminopyrimidine,
4,5-diamino-2-methylamino-6-β-hydroxy-
ethylaminopyrimidine,
5-amino-2,4,5-triethylaminopyrimidine, and
2,4-bis-β-hydroxyethylamino-6-anilino-5-aminopyrimidine.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogenous or pure products. On the contrary, the developer component may consist of mixtures of the developer compounds to be used according to the invention, for example, mixtures of from about 2 to 6 developer compounds, and the coupling substance may be in the form of mixtures of m-phenylenediamine derivatives or salts thereof according to the invention, for example, mixtures of from about 1 to 4 of said compounds. Furthermore, the hair dyestuffs according to the invention may also contain, if desired, conventional, directly applicable dyes in the mixture, provided that such are necessary for the creation of certain color nuances.

The oxidative coupling, that is, the development of the dye, can in principle be carried out with atmospheric oxygen, as is done with other oxidation hair dyestuffs also. However, chemical oxidation agents are advantageously employed. Particularly suitable as such oxidation agents are hydrogen peroxide or its addition compounds with urea, melamine, or sodium borate as well as mixtures of such hydrogen peroxide adducts with potassium peroxydisulfate.

The hair dyes according to the invention are incorporated into respective cosmetic preparations such as creams, emulsions, gels, or also simple solutions for their use and are mixed with one of the mentioned oxidation agents immediately before application to the hair. The concentration of the coupling/developer combination in such dyes is from about 0.2 to 5 percent by weight, preferably from about 1 to 3 percent by weight, based on the total weight of the preparation.

For the preparation of creams, emulsions, or gels, the dye components are mixed with the other components normally used in such preparations. Such additional components include, for example, wetting or emulsifying agents of the anionic or nonionic type such as alkylbenzenesulfonates, sulfates of fatty alcohols, higher alkylsulfonates, alkanolamides of fatty acids, adducts of ethylene oxide onto fatty alchols, thickeners such as methyl cellulose, starch, higher fatty alcohols, paraffin oil, and fatty acids, and perfume oils and hair-conditioning and grooming agents such as pantothenic acid and cholesterol. The mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, on the weight of the total preparation.

A hair dye according to the invention can be applied in a weakly acid, neutral or particularly alkaline medium at a pH of 8 to 10, regardless of whether it is in the form of a solution, an emulsion, a cream, or a gel. The application temperatures range from about 15° to 40° C., preferably at room temperature. After the dye is allowed to react for approximately 30 minutes, the preparation is removed by rinsing from the dyed hair. The hair is washed with a mild shampoo and dried.

The colors that can be achieved with the hair dyes according to the invention cover a broad spectrum of red-brown to dark brown shades, with the use of various developer and coupling components. The colors obtained show good fastness to light, shampooing, and abrasion, and they are easily stripped with reducing agents.

The following examples are intended to illustrate the invention and are not to be construed as limiting the invention thereto.

EXAMPLES

The sodium salts of m-phenylenediamine derivatives of Formula I were prepared in the following manner:

A. Sodium salt of 2,4-diaminophenylacetic acid (K-1)

Five grams of 2,4-dinitrophenylacetic acid were dissolved in a solution of 1.9 gm of sodium hydrogen carbonate in 200 ml water and reduced with hydrogen in the presence of 0.3 gm of palladium on charcoal at room temperature. After completion of the uptake of hydrogen, the catalyst was filtered off, and the filtrate was evaporated in a rotary evaporator at a bath temperature of 30° C. maximum. An amount of 3.5 gm of 2,4-diaminophenylacetic acid sodium salt was obtained.

Analysis: $C_8H_9N_2O_2Na + 1.5\ H_2O$: Calc.: H=5.62; Na=10.69; Found: H=5.30; Na=10.7

IR-spectrum (KBr): carbonyl bands at 1620 and 1423 $cm^{-1}$.

B. Sodium salt of 2,4-diaminophenoxyacetic acid (K-2)

Five grams of 2,4-dinitrophenoxyacetic acid were dissolved in a solution of 1.8 gm of sodium hydrogen carbonate in 200 ml water and reduced with hydrogen in the presence of 0.3 gm of palladium on charcoal. After completion of the hydrogen uptake, the catalyst was filtered off. The filtrate was then evaporated in a rotary evaporator at a bath temperature of 30° C. maximum, after which 2.5 gm of the sodium salt of 2,4-diaminophenoxyacetic acid were obtained.

Analysis: $C_8H_9N_2O_3Na + 1.5\ H_2O$: Calc.: C=41.56; H=5.23; N=12.11; O=31.14; Found: C=41.80; H=4.94; N=12.0; O=31.4

IR-spectrum (KBr): carbonyl bands at 1620 and 1423 $cm^{-1}$.

C. Sodium salt of 3-(2,4-diaminophenyl)-propionic acid (K-3)

(a) Preparation of 3-(2,4-dinitrophenyl)-propionic acid

Twelve grams of 3-phenylpropionic acid were dissolved in 48 ml of concentrated sulfuric acid. A mixture of 24 ml of concentrated sulfuric acid and 12 ml of nitric acid with a specific gravity of 1.52 was added dropwise to the first solution, the temperature being kept below 30° C. After agitation for an additional 3 hours at room temperature, the reaction mixture was poured on ice, removed by suction, washed with water, and dried at 50° C. under vacuum. An amount of 10.6 gm of 3-(2,4- dinitrophenyl)-propionic acid with a melting point of 113°–117° C. was obtained.

(b) Preparation of the sodium salt of 3-(2,4-diaminophenyl)-propionic acid

The 3-(2,4-dinitrophenyl)-propionic acid from step (a) was converted into the sodium salt with sodium hydrogen carbonate and reduced in an aqueous solution using a procedure analogous to that described above in A. Five grams of 3-(2,4-dinitrophenyl)-propionic acid yielded 3.5 grams of sodium salt of 3-(2,4-diaminophenyl)-propionic acid.

Analysis: $C_9H_{11}N_2O_2Na + 2\ H_2O$: Calc.: C=45.38; N=11.76; Found: C=45.4; N=12.1

IR-spectrum: carboxylate bands at 1560 and 1405 $cm^{-1}$.

D. Sodium salt of 2-(2,4-diaminophenoxy)-propionic acid (K-4)

(a) Preparation of 2-(2,4-dinitrophenoxy)-propionic acid

Forty milliliters of nitric acid with a specific gravity of 1.52 were cooled to −5° C. and 9.96 gm of 2-phenoxypropionic acid were added in portions at this temperature. After the addition was complete, the mixture was agitated 10 minutes more at −5° C. and then worked up according to the procedure set forth for C. An amount of 14 gm of 2-(2,4-dinitrophenoxy)-propionic acid with a melting point of 167°–171° C. was obtained.

(b) Preparation of the sodium salt of 2-(2,4-diaminophenoxy)-propionic acid

The 2-(2,4-dinitrophenoxy)-propionic acid from step (a) was converted into the sodium salt with sodium hydrogen carbonate and reduced in aqueous solution, using procedures analogous to those set forth in A, and the sodium salt was then isolated. Five grams of 2-(2,4-dinitrophenoxy)-propionic acid yielded 2.4 gm of sodium salt of 2-(2,4-diaminophenoxy)-propionic acid.

Analysis: $C_9H_{11}N_2O_3Na + 2\ H_2O$: Calc.: C=42.52; H=5.91; Found: C=42.4; H=5.9

IR-spectrum: carboxylate bands at 1600 and 1412 $cm^{-1}$.

E. Sodium salt of 2-(2,4-diaminophenoxy)-butyric acid (K-5)

(a) Preparation of 2-(2,4-dinitrophenoxy)-butyric acid

The synthesis was carried out analogous to the procedure set forth for D, and 12.8 gm of 2-(2,4-dinitrophenoxy)-butyric acid with a melting point of 120°–123° C. were obtained from 10.8 gm of 2-phenoxybutyric acid.

(b) Preparation of the sodium salt of 2-(2,4-diaminophenoxy)-butyric acid

After conversion into the sodium salt, 5.3 gm of 2-(2,4-dinitrophenoxy)-butyric acid were reduced, according to the procedure set for D above, and worked up. An amount of 3.3 gm of sodium salt of 2-(2,4-diaminophenoxy)-butyric acid was obtained.

Analysis: $C_{10}H_{13}N_2O_3Na + 2\ H_2O$: Calc.: C=44.78; N=10.45; Found: C=44.7; N=10.0

IR-spectrum: carboxylate bands at 1600 and 1412 $cm^{-1}$

The above-mentioned m-phenylenediamine derivatives K-1 to K-5, the preparation of which was described, were used as coupling components below. The following substances were used as developer components:

E-1: p-toluylenediammonium sulfate
E-2: N-methyl-p-phenylenediammonium sulfate
E-3: N-ethyl-N-hydroxyethyl-p-phenylenediammonium sulfate
E-4: N-{2-[N-ethyl-N-(4-amino-3-methylphenyl)amino]-ethyl}-methanesulfonamide sesquisulfate(monohydrate)
E-5: N-ethyl-N-(2-hydroxyethyl)-1,4-phenylenediamine sulfate(monohydrate).

Procedure

The hair dyes according to the invention were used in the form of a cream emulsion. For this, 0.01 mol of each of the developer substances and coupling substances listed in the table below were worked into an emulsion containing 10 parts by weight of fatty alcohols having 12 to 18 carbon atoms,
10 parts by weight of fatty alcohol sulfate (sodium salt) having 12 to 18 carbon atoms, and
75 parts by weight of water.

Then the pH of the emulsion was adjusted to 9.5 with ammonia, and the emulsion was made up to 100 parts by weight with water. Oxidative coupling was carried out with a 1% hydrogen peroxide solution acting as oxidation agent, 10 parts by weight of the hydrogen peroxide solution being added to 100 parts by weight of the emulsion. The particular dyeing cream, with additional oxidation agent, was applied to human hair which was 90% grey and which had not been specially pretreated, and the cream was left on the hair for 30 minutes. After completion of the dyeing process, the hair was washed out with a conventional shampoo and dried. The colorations obtained by this process are compiled in the table below.

TABLE I

| Example | Coupling Agent | Developer | Shade Obtained with 1% $H_2O$ Solution |
|---|---|---|---|
| 1 | K-1 | E-1 | black blue |
| 2 | K-1 | E-2 | turquoise |
| 3 | K-2 | E-3 | violet black |
| 4 | K-2 | E-4 | blue black |
| 5 | K-2 | E-5 | blue black |
| 6 | K-2 | E-1 | dark violet |
| 7 | K-3 | E-1 | blue gray |
| 8 | K-4 | E-1 | blue gray |
| 9 | K-5 | E-1 | blue gray |

Comparative Testing

The following coupler components were employed:
(a) 2,4-diaminophenylacetic acid, sodium salt (K-1), and
(b) 2,5-diaminophenylacetic acid, sodium salt (V), prepared by a procedure anologous to that of Example I of Raasch, U.S. Pat. No. 2,603,659.

Coloration Procedure

Hair dye cream emulsions having the following composition were prepared:

| Component | Amount | |
|---|---|---|
| (a) $C_{12-18}$-Fatty alcohol | 10 | gm |
| (b) $C_{12/14}$-Fatty alcohol + EO—sulfate, Na salt (28%) | 25 | gm |
| (c) p-Toluylenediammonium sulfate (developer) | 0.0075 | mol |

-continued

| Component | Amount |
|---|---|
| (d) Coupler A or V | 0.0075 mol |
| (e) Sodium sulfite (inhibitor) | 1.0 gm |
| (f) Conc. NH₄OH solution | to pH = 9.5 |
| (g) Water | q.s. ad 100 gm |

Components (a) and (b) were added to 60 gm of water, after which components (c), (d), and (e) were added. Then, the pH of the emulsion was adjusted to 9.5 by addition of component (f), and sufficient additional water was added to bring the emulsion to 100 gm.

Oxidative coupling was carried out by addition to, and intimate admixture with, the resulting emulsion of 50 gm of 3% hydrogen peroxide solution as oxidation agent. After addition of the oxidation agent, each dye stuff cream was applied to 5 cm strands of standardized human hair which had not been specially pretreated, and the cream was left on the hair for 30 minutes at 35° C. After completion of the dyeing process, the hair was washed with a regular hair shampoo, rinsed, and then dried.

Coupler K-1 and then Coupler V were used with Developers E-1, E-2, and E-4 in the procedure described above. However, in two additional runs Developer E-1 and Coupler V were each used as developer, without coupling agent, to demonstrate the results of "self-coupling".

The results of the above-described testing are set forth in the following table:

TABLE II

| Example No. | Coupler | Developer | Shade obtained with 3% H₂O₂ Solution |
|---|---|---|---|
| 10 | K-1 | E-1 | dark blue |
| 11 | K-1 | E-2 | turquoise |
| 12 | K-1 | E-4 | gray blue |
| 13 | V | E-1 | dark brown |
| 14 | V | E-2 | brown olive |
| 15 | V | E-4 | brown olive |
| 16 | — | E-1 | black-brown |
| 17 | — | Coupler V | sandy |

The use of 2,4-diaminophenyl-acetic acid, Na salt (K-1) as coupling agent in combination with conventional developers led to blue color nuances. However, the use of 2,5-diaminophenyl-acetic acid, Na salt (Coupler V) as coupling agent in combination with conventional developers did not lead to blue color nuances.

The results for Examples 16 and 17 show that no blue color nuance occurs through "self-coupling" of the typical developer p-toluylenediamine (E-1) or 2,5-diaminophenyl-acetic acid. Consequently, the nuance in Example 13 is only the result of "self-coupling" of the 2,5-isomeric compounds.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A method for the dyeing of human hair comprising applying to said hair, at temperatures ranging substantially from about 15° to 40° C. at a pH of from about 8 to 10 for a time sufficient to effect dyeing through oxidation, a hair dyeing effective amount of an oxidation dye composition for dyeing human hair comprising (a) a compound selected from the group consisting of 2,4-diaminophenyl-acetic acid, 2,4-diaminophenoxyacetic acid, and ammonium, alkali metal, and alkaline earth metal salts thereof, or a mixture of two or more of said compounds, as coupler component, and (b) a compound selected from the group consisting of p-phenylenediamine, p-toluylenediamine, N-methyl-p-phenylenediamine, N,N-dimethyl-p-phenylenediamine, N,N-diethyl-p-phenylenediamine, N,N-diethyl-2-methyl-p-phenylenediamine, N-ethyl-N-hydroxyethyl-p-phenylenediamine, N,N-bis-(β-hydroxyethyl)-amino-p-phenylenediamine, methoxy-p-phenylenediamine, 2-chloro-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, p-toluylenediammonium sulfate, N-methyl-p-phenylenediammonium sulfate, N-ethyl-N-hydroxyethyl-p-phenylene-diammonium sulfate, N-[2-[N-ethyl-N-(4-amino-3-methyl-phenyl)-amino]-ethyl]methanesulfonamide sesquisulfate (monohydrate), and N-ethyl-N-(-2-hydroxyethyl)-1,4-phenylenediamine sulfate (monohydrate), or a mixture of two or more of said compounds, as developer component, the molar ratio of component (a) to component (b) being from about 2:1 to 1:2.

2. The method of claim 1, wherein component (b) comprises from 1 to 6 compounds as developer component.

3. The method of claim 1, wherein component (a) comprises from 1 to 4 compounds as coupler component.

4. The method of claim 1, wherein the composition comprises from about 0.2 to 5 percent by weight of developer-coupler combination.

5. The method of claim 4, wherein the composition comprises from about 1 to 3 percent by weight of developer-coupler combination.

* * * * *